United States Patent [19]

Hidaka et al.

[11] Patent Number: 5,244,895
[45] Date of Patent: Sep. 14, 1993

[54] ANTI-ULCER AGENT

[75] Inventors: Hiroyoshi Hidaka, 1101-1-5-104, Hachimanyama, Tenpaku-ku, Nagoya-shi, Aichi; Tomohiko Ishikawa, Nagoya, both of Japan

[73] Assignee: Hiroyoshi Hidaka, Nagoya, Japan

[21] Appl. No.: 883,344

[22] Filed: May 15, 1992

[30] Foreign Application Priority Data

May 15, 1991 [JP] Japan .................................. 1-38580

[51] Int. Cl.$^5$ .................. A61K 31/55; A61K 31/495; C07D 401/00
[52] U.S. Cl. ................................ 514/253; 514/212; 514/218; 514/307; 514/308; 540/575; 540/597; 544/363; 546/140; 546/146; 546/148
[58] Field of Search ................ 544/363; 540/575, 597; 546/140, 146, 148; 514/212, 218, 253, 307, 308

[56] References Cited

U.S. PATENT DOCUMENTS

| | | | |
|---|---|---|---|
| 4,525,589 | 6/1985 | Hidaka et al. | 544/363 |
| 4,632,927 | 12/1986 | Campbell et al. | 544/363 |
| 4,678,783 | 7/1987 | Hidaka et al. | 544/363 |
| 4,758,566 | 7/1988 | Uno et al. | 544/363 |

FOREIGN PATENT DOCUMENTS 3942114 6/1990 Fed. Rep. of Germany .
2640973 6/1990 France .

OTHER PUBLICATIONS

Hidaka et al, Methods Enzymol. 201 (Protein Phosphorylation, pt. B), 328-39 (1991).
Tohda et al, Neurosci. Lett. 129(1), 47-50 (1991).
Ishikawa et al, J. Pharmacol. Exp. Ther. 254(2), 598-602 (1990).
Tokumitsu et al, J. Biol. Chem. 265(8), 4315-20 (1990).
Chemical Abstracts, 68730b, vol. 100, 1984, & JP-58 33 866, p. 642, "Tyrosinol Derivatives".
Chemical Abstracts, 233042m, vol. 112, 1990, p. 399, & J. Biol. Chem. 1990, 265(8), pp. 4315-4320, H. Tokumitsu, et al., "KN-62, 1-[N,O-Bis(5-isoquinolinesulfonyl) —N— Methyl—L—Tyrosyl]—4—Phenylpiperazine, A Specific Inhibitor of Calcium/Calmodulin-Dependent Protein Kinase II".

*Primary Examiner*—Cecilia Tsang
*Attorney, Agent, or Firm*—Oblon, Spivak, McClelland, Maier & Neustadt

[57] ABSTRACT

An anti-ulcer agent contains a compound expressed by the following general formula 1:

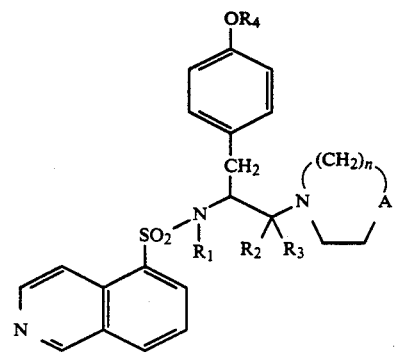

where, $R_1$ is hydrogen atom or an alkyl group having 1 or 2 carbon atoms with or without substitution, $R_2$ and $R_3$ are resp. hydrogen atom or form oxo group together, $R_4$ is hydrogen atom or methyl group or isoquinoline sulfonyl group, n is 2 or 3, A is N—$R_5$ or CH—$R_5$, $R_5$ is phenyl group with or without substitution or benzyloxycarbonyl group with or without substitution, or a physiologically allowable acid added salt thereof as the active component.

10 Claims, No Drawings

ANTI-ULCER AGENT

The present invention relates to an anti-ulcer agent containing a derivative comprising tyrosine as the fundamental chemical structure as the active component.

The peptic ulcer as the representative of ulcers forms by an unbalance between the secretion of gastric juice and the protective mechanism of the digestive tract mucosa against it. Therefore, recently $H_2$-receptor antagonists have been developed and have got excellent results in addition to the conventional antacid agents, antipepsin agents, anticholine agents, antigastrin agents and medical therapies for mucosa protection.

In consideration of the above circumstance, $H_2$-receptor antagonists for peptic ulcer such as 1-cyano-2-methyl-3-[2-[5-methyl-4-imidazolyl)methyl)thio]ethyl]-guanidine compound have given rapid expression of treating effect and high cure rate and also have shown good results for the treatment of intractable ulcers. However, as these $H_2$-receptor antagonists have found wider use, side effects such as the lesion in central nervous system and liver have become to be observed mainly in the agents. In addition, a high recidivation rate has been pointed out after the discontinuation of dosage and the development of a medicine containing a derivative which can improve these problems as a component has come to be considered. The object of the present invention is to solve the problem of side effect of the above medicine while maintaining the excellent cure effect of the conventional $H_2$-receptor antagonists.

In considering the circumstance where unexpected side effect has been found in the $H_2$-receptor antagonists which have been developed as completed anti-ulcer agents, we have investigated a compound exerting an excellent effect with no side effect and have found the first ray of hope in some derivatives comprising tyrosine as the fundamental structure among the compounds we have previously developed and claimed in Japan Patent Application No. 52686 of 1990 as having the effects of vascular smooth muscle relaxation and platelet aggregation inhibition by reacting mainly on the circulating system. Further, we have confirmed the anti-ulcer activity in animal tests and have completed the present invention.

The present invention relates to an anti-ulcer agent containing a compound expressed by the following general formula 1:

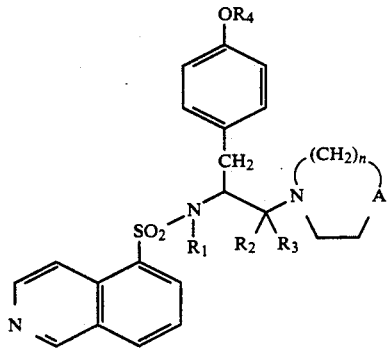

where, $R_1$ is hydrogen atom or an alkyl group having 1 or 2 carbon atoms with or without substitution, $R_2$ and $R_3$ are resp. hydrogen atom or form oxo group together, $R_4$ is hydrogen atom or methyl group or isoquinoline sulfonyl group, n is 2 or 3, A is N—$R_5$ or CH—$R_5$, $R_5$ is phenyl group with or without substitution or benzyloxycarbonyl group with or without substitution.

The typical compounds shown by the general formula 1 according to the present invention include, for example, the following compounds but the present invention is not restricted to these compounds. The number of the compounds are same as in Table 1 and Examples.

(1) N-[1-(p-hydroxybenzyl)-2-(4-phenylpiperazinyl)ethyl]-5-isoquinoline sulfonamide
(2) N-{2-[4-(m-chlorophenyl)piperazinyl]-1-(p-hydroxybenzyl)ethyl}-N-methyl-5-isoquinoline sulfonamide
(3) N-{2-[4-(p-fluorophenyl)piperazinyl]-1-(p-(5-isoquinoline sulfonyloxy)benzyl]ethyl}-5-isoquinoline sulfonamide
(4) N-[2-(4-benzyloxycarbonylpiperazinyl)-1-(p-hydroxybenzyl)ethyl]-N-methyl-5-isoquinoline sulfonamide
(5) N-[2-(4-benzyloxycarbonylpiperazinyl)-1-(p-methoxybenzyl)ethyl]-N-methyl-5-isoquinoline sulfonamide
(6) N-[1-(p-hydroxybenzyl)-2-(4-phenylhomopiperazinyl)ethyl]-5-isoquinoline sulfonamide
(7) N-{1-(p-hydroxybenzyl)-2-[4-(3,4-dichlorobenzyloxy)piperidino]ethyl}-5-isoquinoline sulfonamide
(8) N-{1-(p-hydroxybenzyl)-2-[4-(3,4-dichlorobenzyloxy)piperidino]ethyl}-N-methyl-5-isoquinoline sulfonamide
(9) N-{1-(p-methoxybenzyl)-2-[4-(3,4-dichlorobenzyloxy)piperidino]ethyl}-N-methyl-5-isoquinoline sulfonamide
(10) N-{1-(p-(5-isoquinoline sulfonyloxy)benzyl]-2-(4-phenylpiperidino)ethyl}-N-methyl-5-isoquinoline sulfonamide
(11) N-[1-(p-hydroxybenzyl)-2-(4-phenylpiperidino)ethyl]-N-methyl-5-isoquinoline sulfonamide
(12) N-[N,O-bis(5-isoquinoline sulfonyl)tyrosyl]-4-phenylpiperizine
(13) N-[N,O-bis(5-isoquinoline sulfonyl)-N-methyltyrosyl]-4-phenylpiperizine
(14) N-[2-(4-benzyloxycarbonylhomopiperazinyl)-1-(p-hydroxybenzyl)ethyl]-N-methyl-5-isoquinoline sulfonamide
(15) N-[2-(4-benzyloxycarbonylhomopiperazinyl)-1-(p-methoxybenzyl)ethyl]-N-(2-aminoethyl)-5-isoquinoline sulfonamide
(16) N-[2-(4-benzyloxycarbonylhomopiperazinyl)-1-(p-methoxybenzyl)ethyl]-N-(2-dimethylaminoethyl)-5-isoquinoline sulfonamide.

TABLE 1

| | $R_1$ | $R_2$ | $R_3$ | $R_4$ | n | A |
|---|---|---|---|---|---|---|
| (1) | H | H | H | H | 2 | $NC_6H_5$ |

TABLE 1-continued

| | $R_1$ | $R_2$ | $R_3$ | $R_4$ | n | A |
|---|---|---|---|---|---|---|
| (2) | $CH_3$ | H | H | H | 2 | $N(3\text{-}Cl)C_6H_4$ |
| (3) | H | H | H | $SO_2\text{-}5\text{-iq}$ | 2 | $N(4\text{-}F)C_6H_4$ |
| (4) | $CH_3$ | H | H | H | 2 | $NCO_2CH_2C_6H_5$ |
| (5) | $CH_3$ | H | H | $CH_3$ | 2 | $NCO_2CH_2C_6H_5$ |
| (6) | H | H | H | H | 3 | $NC_6H_5$ |
| (7) | H | H | H | H | 2 | $CHOCH_2(3,4\text{-}Cl)C_6H_3$ |
| (8) | $CH_3$ | H | H | H | 2 | $CHOCH_2(3,4\text{-}Cl)C_6H_3$ |
| (9) | $CH_3$ | H | H | $CH_3$ | 2 | $CHOCH_2(3,4\text{-}Cl)C_6H_3$ |
| (10) | $CH_3$ | H | H | $SO_2\text{-}5\text{-iq}$ | 2 | $CHC_6H_5$ |
| (11) | $CH_3$ | H | H | H | 2 | $CHC_6H_5$ |
| (12) | H | | =O | $SO_2\text{-}5\text{-iq}$ | 2 | $NC_6H_5$ |
| (13) | $CH_3$ | | =O | $SO_2\text{-}5\text{-iq}$ | 2 | $NC_6H_5$ |
| (14) | $CH_3$ | H | H | H | 3 | $NCO_2CH_2C_6H_5$ |
| (15) | $CH_2CH_2NH_2$ | H | H | $CH_3$ | 3 | $NCO_2CH_2C_6H_5$ |
| (16) | $CH_2CH_2N(CH_3)_2$ | H | H | $CH_3$ | 3 | $NCO_2CH_2C_6H_5$ | where 5-iq means 5-isoquinoline.

The acid-added salts of the isoquinoline sulfonic acid derivatives expressed by the above general formula 1 include, for example, their salts of an inorganic acid such as phosphoric acid, hydrochloric acid and sulfuric acid and of an organic acid such as acetic acid, citric acid, succinic acid, fumaric acid and tartaric acid.

The compound expressed by the general formula 1 according to the present invention can be synthesized by the method described in Japan Patent Application No. 52686 of 1990. The method for the preparation of the compound according to the present invention described in the Specification is as follows in brief.

Piperazine in which one of the nitrogens is protected was reacted with tyrosine of the following general formula 2 in which the amino group is protected, a known compound:

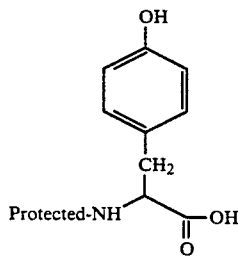

to prepare a compound of the following general formula 3:

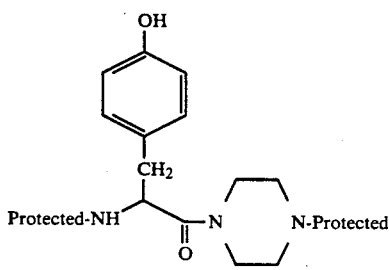

and the protective group for the amino group in the compound was removed and the resultant free amino compound was condensed with isoquinoline sulfonyl chloride to prepare a compound of the following general formula 4:

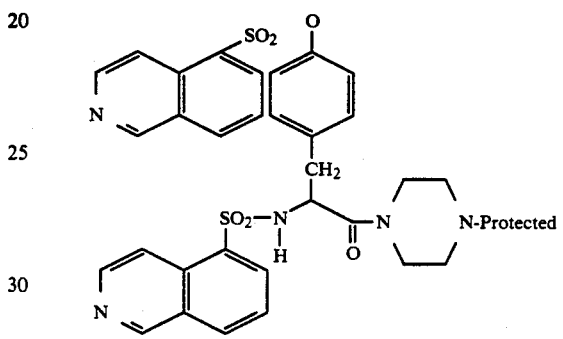

If required, some of the compounds according to the present invention can be prepared by subjecting the compound of the formula 4 to at least one of the procedures including:

(a) A step of making the hydroxyl group free
(b) A step of removing the protective groups for piperazine
(c) A step of alkylating the free hydroxyl group
(d) A step of acylating the piperazine
(e) A step of alkylating or substituted-alkylating the sulfonamide.

Piperidine or homopiperazine can be also used in place of the piperazine used in the above example. The compound of the general formula 2 may be alkylated at the protected amino group or may be protected at the hydroxyl group. The compound of the general formula 3 may be reduced at the stage to convert carbonyl to methylene chain.

The Preparative Examples of the above-mentioned compound (7), (13) and (15) will be illustrated as follows.

PREPARATIVE EXAMPLE 1

Compound (7)

13.39 g of N-t-butoxycarbonyltyrosine methyl ester was dissolved in 65 ml of tetrahydrofuran and 65 ml of dimethylformamide. 1.9 g of 60% sodium hydride was added to the solution under stirring while ice-cooled. After the ice bath was removed, the mixture was stirred at room temperature for 30 minutes and then 5.4 g of methoxyethoxymethyl chloride was added while ice-cooled again and the temperature of the mixture was stirred for 15 hours while the temperature was restored to room temperature gradually. The reaction liquor was poured into ice water and saturated by sodium chloride and extracted with each 800 ml of chloroform twice. The extract was dried on magnesium sulfate and the solvent was distilled off in vacuo and the resultant residue was fed to a silica gel column and eluted by hexane-ethyl acetate (4:1) to give 13.85 g of the colorless amorphous object. It was dissolved in 90 ml of ethanol and 60 ml of tetrahydrofuran. 3.11 g of lithium chloride and 2.77 g of sodium borohydride were added under stirring while ice-cooled and then the ice bath was removed and the mixture was stirred at room temperature for 16 hours and then saturated saline water was added and the nature of the solution was made alkaline with sodium bicarbonate and then the solution was extracted with each 800 ml of chloroform twice. The extract was dried on magnesium sulfate and the solvent was distilled off in vacuo to give 11.73 g of N-t-butoxycarbonyl-o-(2-methoxyethoxymethyl)tyrosinol. It was dissolved in 120 ml of carbon tetrachloride. 10 g of triphenylphosphine was added to the solution and the solution was refluxed by heating for 3 hours and then heated at 80° C. for 17 hours. The solvent was distilled off in vacuo and the residue was fed to a silica gel column and eluted by chloroform-methanol (100:1) and then by hexane-ethyl acetate (4:1) to give the objective chloro compound. 1.56 g of the chloro compound was dissolved in 25 ml of dimethylformamide. 1.08 g of 4-(3,4-dichlorobenzyloxy) piperidine, 0.67 g of potassium carbide and 0.67 g of sodium iodide were added to the solution and the mixture was stirred at 100° C. for 2 hours and saturated saline water was added to it and then the mixture was extracted with each 150 ml of chloroform twice. The extract was dried on magnesium sulfate and the solvent was distilled off in vacuo and the residue was fed to a silica gel column and eluted by chloroform-methanol (100:1) to give 1.53 g of the colorless amorphous object. It was dissolved in 5 ml of methyl acetate. 15 ml of 3N hydrochloric acid ethyl acetate solution was added to the solution at room temperature under stirring and then the mixture was stirred for 1 hour and the solvent was distilled off in vacuo. The resultant residue was dissolved in water and the nature of the solution was made alkaline with sodium bicarbonate and the solution was saturated by sodium chloride and washed with small amount of methanol and extracted with each 100 ml of chloroform twice and dried on magnesium sulfate and the solvent was distilled off in vacuo to give 819 mg of N-[2-amino-3(p-hydroxyphenyl)]propyl-4-(3,4-dichlorobenzyloxy)piperidine. The whole amount of it was dissolved in 20 ml of tetrahydrofuran. 1.16 g of 5-isoquinoline sulfonyl chloride monohydrochloride and then 904 ml of triethylamine were added to the solution successively under stirring while ice-cooled and the mixture was stirred for 18 hours and then the nature of the solution was made alkaline with sodium bicarbonate and the solution was extracted with each 100 ml of chloroform twice. The extract was dried on magnesium sulfate and concentrated in vacuo and the resultant residue was fed to a silica gel column and eluted by chloroform-methanol (30:1) to give 1.13 g of colorless amorphous product. 700 mg of it was dissolved in 2.5 ml of methanol and 2.5 ml of tetrahydrofuran. 8 ml of 1N caustic soda solution was added to the solution and the mixture was refluxed by heating for 2 hours. After cooled, the reaction liquor was diluted with water and the nature of the solution was once made acid with citric acid and then made alkaline with sodium bicarbonate and the solution was extracted with each 100 ml of chloroform twice and the extract was dried on magnesium sulfate and concentrated in vacuo and the resultant residue was fed to a silica gel column and eluted by chloroform-methanol (20:1) to give 418 mg of the objective product.

IR (KBr)cm$^{-1}$: 1615, 1375, 1130, 860.

$^1$H-NMR(CDCl$_3$, δ ppm): 1.2–1.8 (4H, m), 1.9–2.2 (2H, m), 2.2–2.6 (4H, m), 2.62 (1H, dd, J=14.28, 6.85 Hz), 2.75 (1H, dd, J=14.28, 6.28 Hz), 3.29 (2H, m), 4.33 (2H, br), 4.39 (2H, s), 6.38 (2H, d,J=8.57 Hz), 6.67 (2H, d, J=8.57 Hz), 7.12 (1H, dd, J=8.57, 1.71 Hz), 7.38 (1H, d, J=8.57 Hz), 7.39 (1H, d, J=1.71 Hz), 7.67 (1H, t, J=7.42 Hz), 8.20 (1H, d, J=7.42 Hz), 8.37 (1H, d, J=6.28 Hz), 8.40 (1H, dd, J=7.42, 1.0 Hz), 8.58 (1H, d, J=6.28 Hz), 9.3 (1H, s).

PREPARATIVE EXAMPLE 2

Compound (13)

12.3 g of N-benzyloxycarbonyltyrosine and 6.6 g of N-phenylpiprazine were dissolved in 150 ml of methylene chloride. 8.4 g of DCC was added to the solution and the mixture was stirred at room temperature for 5 hours. The deposited insoluble was filtered off and the filtrate was concentrated in vacuo and the resultant residue was fed to a silica gel column and eluted by hexane-ethyl acetate (1:1 to 1:2) to give 10.5 g of colorless amorphous product. 4.59 g of it was dissolved in 50 ml of methanol. 3 g of 5% palladium carbon was added to the solution and the mixture was stirred at room temperature for 17 hours under hydrogen atmosphere. The insoluble formed was filtered off and the filtrate was concentrated in vacuo and the residue was suspended in 50 ml of chloroform. 5.8 g of 5-isoquinoline sulfonyl chloride monohydrochloride and then 10 ml of triethylamine were added to the suspension successively and the mixture was stirred at room temperature for 3 hours. After 200 ml of water was added to reaction liquor, it was extracted with each 100 ml of chloroform twice and dried on magnesium sulfate and concentrated in vacuo and the resultant residue was fed to a silica gel column and eluted by chloroform methanol (80:1 to 30:1) to give 5.46 g of yellow amorphous product.

2.27 g of it was dissolved in dimethylformamide and 160 mg of 60% sodium hydride and 0.3 ml of methyl iodide were added successively while ice-cooled and the mixture was stirred for 1 hour and a half while ice-cooled. 80 ml of water was added to the reaction liquor and then it was washed with 100 ml of ethyl acetate and dried on magnesium sulfate and concentrated in vacuo and the resultant residue was fed to a silica gel column and eluted by chloroform-methanol (60:1) to give 1.8 g of the yellow amorphous object.

IR(KBr)cm$^{-1}$: 1668, 1475, 1360, 1130.

$^1$H-NMR(CDCl$_3$, δ ppm): 2.45 (1H, dd, J=4.6, 13.1 Hz), 2.63 (1H, m),2.82–3.07 (4H, m), 3.03 (3H, s), 3.13–3.29 (2H, m), 3.43–3.65 (4H, m), 5.11 (1H, dd, J=4.6, 10.3 Hz), 6.76 (2H, d, J=8.6 Hz), 6.85 (2H, d, J=8.0 Hz), 6.88 (1H, t, J=8.6 Hz), 7.29 (2H, dd, J=8.0, 8.6 Hz), 7.49 (1H, dd, J=8.3, 7.3 Hz), 7.70 (1H, dd, J=8.3, 7.3 Hz), 8.16 (1H, dd, J=1.0, 7.3 Hz), 8.21 (2H, d, J=8.3 Hz), 8.30 (1H, dd, J=1.0, 7.3 Hz), 8.41 (1H, d, J=6.4 Hz), 8.51 (1H, d, J=6.4 Hz), 8.68 (1H, d, J=6.4 Hz), 8.80 (1H, d, J=6.4 Hz), 9.36 (1H, s), 9.40 (1H, s).

PREPARATIVE EXAMPLE 3

Compound (15)

1.0 g of N-[2-(4-benzyloxycarbonylpiperazinyl)-1-(p-methoxybenzyl)ethyl]-5-isoquinoline sulfonamide was dissolved in 5 ml of tetrahydrofuran. 685 mg of triphenylphosphine and 340 mg of N-t-butoxycarbonylethanolamine were added to the solution and 3 ml of tetrahydrofuran solution of 530 mg of diisopropylazodicarboxylate was dropped to it under stirring while ice-cooled. The ice bath was removed and the reaction liquor was stirred at room temperature for 3 hours and then poured into water and the nature of the solution was made alkaline with sodium bicarbonate and the solution was extracted with each 150 ml of chloroform twice and the extract was dried on magnesium sulfate and the solvent was distilled off in vacuo.

The resultant oil was dissolved in 2 ml of ethyl acetate. 30 ml of 4N hydrochloric acid/ethyl acetate solution was added to it and the mixture was stirred at room temperature for 30 minutes and then 100 ml of 1N hydrochloric acid was added to it and the mixture was washed with ethyl acetate twice and the aqueous layer was made alkaline with sodium bicarbonate and extracted with each 150 ml of chloroform twice. The extract was dried on magnesium sulfate and the solvent was distilled off in vacuo and the resultant oil was fed to a silica gel column and 400 mg of the colorless amorphous object was obtained from a fraction eluted by chloroform-methanol (100:1 to 50:1).

IR(KBr)cm$^{-1}$: 1701, 1514, 1325, 1248, 1135, 763, 601.

$^1$H-NMR(CDCl$_3$, δ ppm): 1.99 (2H, brs), 2.15–2.40 (5H, m), 2.55–2.80 (3H, m), 2.90–3.10 (2H, m), 3.20–3.70 (6H, m), 3.73 (3H, s), 4.98 (1H, m), 5.10 (2H, s), 6.54 (2H, d, J=8.55 Hz), 6.77 (2H, d, J=8.55 Hz), 7.33 (5H, s), 7.62 (1H, dd, J=8.06, 7.57 Hz), 8.14 (1H, d, J=8.06 Hz), 8.34 (1H, d, J=6.10 Hz), 8.39 (1H, d, J=7.57 Hz), 8.63 (1H, d, J=6.10 Hz), 9.28 (1H, s).

EXAMPLES

The compounds according to the present invention are shown to have the properties of medical values as anti-ulcer agents by the following tests. The numbers of Examples correspond to the numbers of the compounds mentioned above.

Anti-gastric Juice Secretion Test

1. Intraduodenal Administration

Each 100 mg/kg of the test compounds was administered duodenally to a male Crj:Wistar rat of 205 to 240 g body weight fasted for ca. 24 hours (7 to 8 rats per group) and immediately after the dose the pylorus was ligated under diethyl ether anesthesia. Four hours after the ligation, the animal was killed and the stomach was isolated and the amount and the pH of gastric juice and free hydrochloric acid contained in it and the total acidity of it were measured to examine the effect of inhibiting gastric juice secretion. The test compounds were dosed after dissolved in physiological saline or in physiological saline containing Tween 80 added. Five mg/kg of physiological saline was administered to the control group. The results are shown in Table 2.

TABLE 2

| No. of example | Amount of gastric juice (ml/100 g body weight) | pH | Free hydrochloric acid (μEq/100 body weight) | Total acidity (μEq/100 body weight) |
| --- | --- | --- | --- | --- |
| Control group | 2.6 | 1.7 | 116 | 168 |
| (1) | 2.2 | 2.0 | 36 | 71 |
| (2) | 2.1 | 2.1 | 40 | 92 |
| (3) | 2.5 | 1.8 | 82 | 140 |
| (4) | 1.8 | 2.3 | 36 | 74 |

TABLE 2-continued

| No. of example | Amount of gastric juice (ml/100 g body weight) | pH | Free hydrochloric acid (μEq/100 body weight) | Total acidity (μEq/100 body weight) |
| --- | --- | --- | --- | --- |
| (5) | 1.8 | 2.3 | 48 | 80 |
| (6) | 2.3 | 1.8 | 53 | 87 |
| (7) | 1.2 | 2.5 | 26 | 63 |
| (8) | 1.6 | 2.3 | 32 | 68 |
| (9) | 2.2 | 2.1 | 44 | 89 |
| (10) | 2.4 | 1.8 | 68 | 102 |
| (11) | 1.5 | 2.5 | 36 | 65 |
| (12) | 2.2 | 2.1 | 41 | 80 |
| (13) | 1.9 | 2.3 | 42 | 78 |
| (14) | 0.6 | 3.1 | 8 | 11 |
| (15) | 1.1 | 2.6 | 22 | 43 |
| (16) | 0.9 | 2.9 | 11 | 29 |

2. Intraperitoneal Administration

Each 100 mg/kg of the test compounds was administered intraperitoneally to a male Crj:Wistar rat of 196 to 232 g body weight fasted for ca. 24 hours (6 to 7 rats per group) and 30 minutes after the administration the pylorus was ligated under diethyl ether anesthesia. The test was performed in a same manner as in the duodenal administration test. The results are shown in Table 3.

TABLE 3

| No. of example | Amount of gastric juice (ml/100 g body weight) | pH | Free hydrochloric acid (μEq/100 body weight) | Total acidity (μEq/100 body weight) |
| --- | --- | --- | --- | --- |
| Control group | 3.2 | 1.7 | 155 | 208 |
| (7) | 1.5 | 2.6 | 32 | 71 |
| (13) | 1.6 | 2.4 | 55 | 102 |
| (14) | 0.6 | 3.0 | 4 | 17 |
| (15) | 1.3 | 2.6 | 36 | 74 |
| (16) | 0.6 | 2.9 | 8 | 24 |

Anti-Aspirin Ulcer Test

1. Oral Administration

Each 100 mg/kg of the test compounds was administered orally to a male Crj:Wistar rat of 198 to 243 g body weight fasted for ca. 24 hours (7 to 8 rats per group) and 30 minutes after the administration 200 mg/5 ml/kg of aspirin suspended in 0.5% sodium CMC aqueous solution was administered orally. Six hours later the animals was killed by exsanguination and the cardia part of stomach was ligated and 10 ml of 1% formaline solution was poured into the stomach and the stomach was extirpated. Then, it was incised along the greater curvature side and washed with physiological saline and the major axis of the spotted and linear erosion and ulcer were measured under a steromicroscope and their total sum per head was calculated as the gastric damage index (mm) and the effect was judged by the inhibiting rate against the control group [(Gastric damage index of the control group−Gastric damage index of the test compound)/Gastric damage index of the control group×100]. 0.5 ml/body weight of 1% pontamine sky blue physiological saline was injected intravenously 10 minutes before the slaughter. The test compound was administered after dissolved in physiological saline or in physiological saline containing Tween 80 added. Five mg/kg of physiological saline was administered to the control group. The results are shown in Table 4.

TABLE 4

| No. of example | Gastric damage index (mm) | Inhibition rate (%) |
| --- | --- | --- |
| Control group | 76.0 | — |
| (1) | 40.1 | 47 |
| (2) | 40.3 | 46 |
| (3) | 56.7 | 25 |
| (4) | 34.6 | 55 |
| (5) | 36.5 | 53 |
| (6) | 52.9 | 30 |
| (7) | 26.9 | 65 |
| (8) | 28.9 | 62 |
| (9) | 45.4 | 40 |
| (10) | 48.3 | 37 |
| (11) | 27.3 | 64 |
| (12) | 43.5 | 43 |
| (13) | 30.3 | 60 |
| (14) | 11.2 | 85 |
| (15) | 35.8 | 64 |
| (16) | 17.0 | 78 |

2. Intraperitoneal Administration

Each 100 mg/kg of the test compound was abdominally injected to a male Crj:Wistar rat of 210 to 265 g body weight fasted for ca. 24 hours (7 to 8 rats per group) and the procedures were carried out in a same manner as in oral administration. The results are shown in Table 5.

TABLE 5

| No. of example | Gastric damage index (mm) | Inhibition rate (%) |
| --- | --- | --- |
| Control group | 58.8 | — |
| (7) | 15.3 | 74 |
| (13) | 17.6 | 70 |
| (14) | 5.3 | 91 |
| (15) | 11.8 | 80 |
| (16) | 10.6 | 82 |

Water Immersion Restriction Stress Ulcer

1. Oral Administration

Each 100 mg/kg of the test compound was orally administered to a male Crj:Wistar rat of 225 to 271 g body weight fasted for ca. 24 hours (7 to 8 rats per group) and 30 minutes after the administration and animal was immersed in water in a constant temperature bath held at 22°±1° C. by using a stress cage to the xipheid to load stress for 6 hours. After the stress loading, the animal was killed by exsanguination and the cardia part of stomach was ligated and then 10 ml of 1% formalin was poured into the stomach and the stomach was extirpated. Then, it was incised along the greater curvature side and washed with physiological saline and the major axis of the spotted and linear erosion and ulcer were measured under a stereomicroscope and their total sum per head was calculated as the gastric damage index (mm) and the effect was judged by the inhibiting rate against the control group [(Gastric damage index of the control group-Gastric damage index of the test compound)/Gastric damage index of the control group×100]. 0.5 ml/body weight of 1% pontamine sky blue physiological saline was injected intravenously 10 minutes before the slaughter. The test compound was administered after dissolved in physiological saline or in physiological saline containing Tween 80 added. Five mg/kg of physiological saline was administered to the control group. The results are shown in Table 6.

TABLE 6

| No. of example | Gastric damage index (mm) | Inhibition rate (%) |
| --- | --- | --- |
| Control group | 15.7 | — |
| (1) | 10.5 | 33 |
| (2) | 9.7 | 38 |
| (3) | 11.2 | 29 |
| (4) | 8.4 | 46 |
| (5) | 7.7 | 51 |
| (6) | 12.2 | 22 |
| (7) | 5.4 | 66 |
| (8) | 6.5 | 59 |
| (9) | 9.7 | 38 |
| (10) | 11.2 | 29 |
| (11) | 6.8 | 57 |
| (12) | 9.4 | 40 |
| (13) | 5.4 | 66 |
| (14) | 4.3 | 73 |
| (15) | 6.6 | 58 |
| (16) | 4.6 | 70 |

2. Intraperitoneal Administration

Each 100 mg/kg of the test compound was intraperitoneally injected to a male Crj:Wistar rat of 233 to 285 g body weight fasted for ca. 24 hours (7 to 8 rats per group) and the procedures were carried out in a same manner as in oral administration. The results are shown in Table 7.

TABLE 7

| No. of example | Gastric damage index (mm) | Inhibition rate (%) |
| --- | --- | --- |
| Control group | 22.7 | — |
| (7) | 7.0 | 69 |
| (13) | 6.4 | 72 |
| (14) | 3.9 | 83 |
| (15) | 6.6 | 71 |
| (16) | 5.4 | 76 |

Toxicity

Each test compound was administered to a male Sle-:ICR mouse of 29 to 32 g body weight fasted for 18 to 20 hours (5 mice per group) to examine the presence of acute toxicity.

As the result, no death was observed in 6 hours observation for 300 to 500 mg/kg oral administration of the test compound in Examples and 200 mg/kg intraperitoneal injection. The results are shown in Tables 8 and 9.

TABLE 8

| | Oral administration | | |
| --- | --- | --- | --- |
| No. of example | Dose (mg/kg) | General condition | Mortality rate |
| (1) | 300 | No abnormality | 0/5 |
| (2) | 300 | No abnormality | 0/5 |
| (3) | 300 | No abnormality | 0/5 |
| (4) | 300 | No abnormality | 0/5 |
| (5) | 300 | No abnormality | 0/5 |
| (6) | 500 | No abnormality | 0/5 |
| (7) | 500 | No abnormality | 0/5 |
| (8) | 300 | No abnormality | 0/5 |
| (9) | 300 | No abnormality | 0/5 |
| (10) | 300 | No abnormality | 0/5 |
| (11) | 500 | No abnormality | 0/5 |
| (12) | 300 | No abnormality | 0/5 |
| (13) | 300 | No abnormality | 0/5 |
| (14) | 300 | No abnormality | 0/5 |
| (15) | 300 | No abnormality | 0/5 |
| (16) | 300 | No abnormality | 0/5 |

TABLE 9

| No. of example | Intraperitoneal administration | | |
|---|---|---|---|
| | Dose (mg/kg) | General condition | Mortality rate |
| (7) | 200 | No abnormality | 0/5 |
| (13) | 200 | No abnormality | 0/5 |
| (14) | 200 | No abnormality | 0/5 |
| (15) | 200 | No abnormality | 0/5 |
| (16) | 200 | No abnormality | 0/5 |

The dose forms of the compounds according to the present invention include, for example, oral administration by tablet, capsule, granule, powder or syrup and nonoral dose by injection and suppository. These medical preparations can be prepared by the known methods by using vehicles, binders, collapsing agents, lubricants, stabilizers and taste improvers. The dosage may be different by the symptom and the age of the patient and 0.01 to 20 mg/kg per day can be usually administered to an adult once or several times a day.

The examples of medical preparations by using the compounds according to the present invention will be shown as follows.

1. Tablet

The following ingredients can be mixed together by a known method to prepare a tablet preparation.

| Ingredients | Amount |
|---|---|
| Compound (13) phosphate | 20 mg |
| Crystalline cellulose | 20 mg |
| Lactose | 65 mg |
| Corn starch | 28.5 mg |
| Magnesium stearate | 1.5 mg |
| Calcium carboxymethylcellulose | 5 mg |
| | 140.0 mg |

2. Aseptic Injection Preparation

The following ingredients is mixed together by a known method to a total of 2 ml and the mixture is filled in an ampule and sealed and sterilized by heating to prepare an aseptic injection preparation.

| Ingredients | Amount |
|---|---|
| Compound (13) phosphate | 20 mg |
| Sodium chloride | 12 mg |
| Distilled water | Appropriate amount |
| | To a total of 2 ml |

The usefulness of the compound according to the present invention as an anti-ulcer agent is obvious from the above Tables 2 to 9.

We claim:

1. A compound of the formula (I):

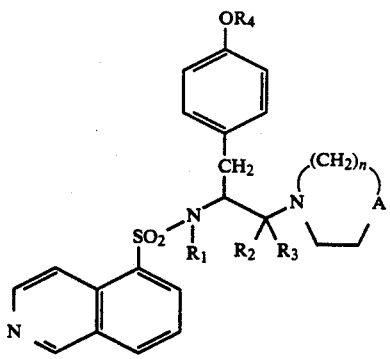

wherein $R_1$ is hydrogen, methyl, ethyl, 2-aminoethyl or 2-dimethylaminoethyl; $R_2$ and $R_3$ are each hydrogen or together form a carbonyl group; $R_4$ is hydrogen or methyl; n is 2 or 3; and A is N—$R_5$ or CH—$R_5$, wherein $R_5$ is —$C_6H_5$—, —(3—Cl)$C_6H_4$, —$CO_2CH_2C_6H_5$ or —$OCH_2$(3, 4—Cl)$C_6H_3$; or a pharmaceutically acceptable salt thereof.

2. The compound of claim 1, which is selected from the group consisting of N(1-(p-hydroxybenzyl)-2-(4-phenylpiperazinyl) ethyl)-5-isoquinoline sulfonamide, N-(2-(4-(m-chlorophenyl)piperazinyl)-1-(p-hydroxybenzyl)ethyl)-N-methyl-5-isoquinoline sulfonamide, N-(2-(4-benzyloxycarbonylpiperazinyl)-1-(p-hydroxybenzyl)ethyl)-N-methyl-5-isoquinoline sulfonamide, N-(2-(4-benzyloxycarbonylpiperazinyl)-1-(p-methoxybenzyl)ethyl)-N-methyl-5-isoquinoline sulfonamide, N-(p-hydroxybenzyl)-2-(4-phenylhomopiperazinyl)ethyl)-5-isoquinoline sulfonamide, N-(1-(p-hydroxybenzyl)-2-(4-(3-dichlorobenzyloxy)piperidino)ethyl)-5-isoquinoline sulfonamide, N-(1-(p-hydroxybenzyl)-2-(4-(3,4-dichlorobenzyloxy)piperidino)ethyl)-N-methyl-5-isoquinoline sulfonamide, N-(1-(p-methoxybenzyl)-2-(4-(3,4-dichlorobenzyloxy)piperidino)ethyl)-N-methyl-5-isoquinoline sulfonamide, N-(1-(p-hydroxybenzyl)-2-(4-phenylpiperidino)ethyl)-N-methyl-5-isoquinoline sulfonamide, N-(2-(4-benzyloxycarbonylhomopiperazinyl)-1-(p-hydroxybenzyl)ethyl)-N-methyl-5-isoquinoline sulfonamide, N-(2-(4-benzyloxycarbonylhomopiperazinyl)-1-(p-methoxybenzyl)ethyl)-N-(2-aminoethyl)-5-isoquinoline sulfonamide, and N-(2-(4-benzyloxycarbonylhomopiperazinyl)-1-(p-methoxybenzyl)ethyl)-N-(2-dimethylaminoethyl)-5-isoquinoline sulfonamide.

3. The compound of claim 1, wherein the salt is a salt of phosphoric acid, hydrochloric acid, sulfuric acid, acetic acid, citric acid, succinic acid, fumaric acid and tartaric acid.

4. An anti-ulcer pharmaceutical composition, which comprises:

a) an effective amount of a compound of the formula (I):

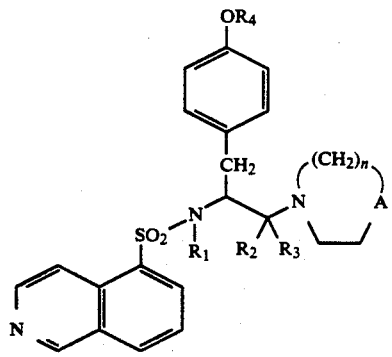

wherein $R_1$ is hydrogen, methyl, ethyl, 2-aminoethyl or 2-dimethylaminoethyl; $R_2$ and $R_3$ are each hydrogen or together form a carbonyl group; $R_4$ is hydrogen or methyl; n is 2 or 3; A is N—$R_5$ or CH—$R_5$, $R_5$ is —$C_6H_5$, $(3-Cl)C_6H_4$, $(4-F)C_6H_4$, —$CO_2CH_2C_6H_5$ or —$OCH_2(3,4-Cl)C_6H_3$; or a pharmaceutically acceptable salt thereof; and b) a pharmaceutically acceptable excipient.

5. The composition of claim 4, wherein said compound of the formula (I) is selected from the group consisting of the group consisting of N(1-(p-hydroxybenzyl)-2-(4-phenylpiperazinyl)ethyl)-5-isoquinoline sulfonamide, N-(2-(4-(m-chlorophenyl)piperazinyl)-1-(p-hydroxybenzyl)ethyl)-N-methyl-5-isoquinoline sulfonamide, N-(2-(4-benzyloxycarbonylpiperazinyl)-1-(p-hydroxybenzyl)ethyl)-N-methyl-5-isoquinoline sulfonamide, N-(2-(4-benzyloxycarbonylpiperazinyl)-1-(p-methoxybenzyl)ethyl)-N-methyl-5-isoquinoline sulfonamide, N-(1-(p-hydroxybenzyl)phenyl)homopiperazinyl)ethyl)-5-isoquinoline sulfonamide, N-(1-(p-hydroxybenzyl)-2-(4-(3,4-dichlorobenzyloxy)piperidino)ethyl)-5-isoquinoline sulfonamide, N-(1-(p-hydroxybenzyl)-2-(4-(3,4-dichlorobenzyloxy)piperidino)ethyl)-N-methyl-5-isoquinoline sulfonamide, N-(1-(p-methoxybenzyl)-2-(4-(3,4-dichlorobenzyloxy)piperidino)ethyl)-N-methyl-5-isoquinoline sulfonamide, N-(1-(p-hydroxybenzyl)-2-(4-phenylpiperidino)ethyl)-N-methyl-5-isoquinoline sulfonamide, N-(2-(4-benzyloxycarbonylhomopiperazinyl)-1-(p-hydroxybenzyl)ethyl)-N-methyl-5-isoquinoline sulfonamide, N-(2-(4-benzyloxycarbonylhomopiperazinyl)-1-(p-methoxybenzyl)ethyl)-N-(2-aminoethyl)-5-isoquinoline sulfonamide, and N-(2-(4-benzyloxycarbonylhomopiperazinyl)-1-(p-methoxybenzyl)ethyl)-N-(2-dimethylaminoethyl)-5-isoquinoline sulfonamide.

6. The composition of claim 4, wherein the salt is a salt of phosphoric acid, hydrochloric acid, sulfuric acid, acetic acid, citric acid, succinic acid, fumaric acid and tartaric acid.

7. A method of preventing or treating peptic ulcers in a mammal, which comprises administering to said mammal an effective amount of a compound of the formula (I):

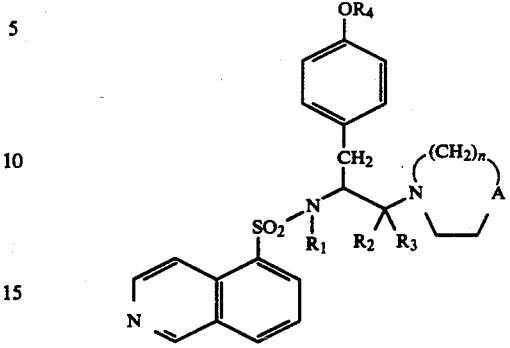

wherein $R_1$ is hydrogen, methyl, ethyl, 2-aminoethyl or 2-dimethylaminoethyl; $R_2$ and $R_3$ are each hydrogen or together form a carbonyl group; $R_4$ is hydrogen, methyl or isoquinoline sulfonyl; n is 2 or 3; A is N—$R_5$ or CH—$R_5$, $R_5$ is —$C_6H_5$, $(3-Cl)C_6H_4$, $(4-F)C_6H_4$, $CO_2CH_2C_6H_5$ or —$OCH_2(3,4-Cl)C_6H_3$; or a pharmaceutically acceptable salt thereof.

8. The method of claim 7, wherein said compound of the formula (I) is selected from the group consisting of N(1-(p-hydroxybenzyl)-2-(4-phenylpiperazinyl)ethyl-5-isoquinoline sulfonamide, N-(2-(4-(m-chlorophenyl)-piperazinyl)-1-(p-hydroxybenzyl)ethyl)-N-methyl-5-isoquinoline sulfonamide, N-(2-(4-benzyloxycarbonylpiperazinyl)-1 -(p-hydroxybenzyl)ethyl)-N-methyl-5-isoquinoline sulfonamide, N-(2-(4-benzyloxycarbonylpiperazinyl)-1-(p-methoxybenzyl)ethyl)-N-methyl-5-isoquinoline sulfonamide, N-(1-p-hydroxybenzyl)-2-(4-phenylhomopiperazinyl)ethyl)-5-isoquinoline sulfonamide, N-(1-(p-hydroxybenzyl)-2-(4-(3,4-dichlorobenzyloxy)piperidino)ethyl)-5-isoquinoline sulfonamide, N-(1-(p-hydroxybenzyl)-2-(4-(3,4-dichlorobenzyloxy)-piperidino)ethyl)-N-methyl-5-isoquinoline sulfonamide, N-(1-(p-methoxybenzyl)-2-(4-(3,4-dichlorobenzyloxy)-piperidino)ethyl)-N-methyl-5-isoquinoline sulfonamide, N-(1-(p-hydroxybenzyl)-2-(4-phenylpiperidino)ethyl)-N-methyl-5-isoquinoline sulfonamide, N-(2-(4-benzyloxycarbonylhomopiperazinyl)-1-(p-hydroxybenzyl)ethyl)-N-methyl-5-isoquinoline sulfonamide, N-(2-(4-benzyloxycarbonylhomopiperazinyl)-1-(p-methoxybenzyl)ethyl)-N-(2-aminoethyl)-5-isoquinoline sulfonamide, and N-(2-(4-benzyloxycarbonylhomopiperazinyl)-1-(p-methoxybenzyl)ethyl)-N-(2-dimethylaminoethyl)-5-isoquinoline sulfonamide.

9. The method of claim 7, wherein the salt is a salt of phosphoric acid, hydrochloric acid, sulfuric acid, acetic acid, citric acid, succinic acid, fumaric acid and tartaric acid.

10. The method of claim 7, wherein said mammal is a human.

* * * * *